United States Patent [19]

Primus et al.

[11] Patent Number: 4,818,709

[45] Date of Patent: Apr. 4, 1989

[54] CEA-FAMILY ANTIGENS, ANTI-CEA ANTIBODIES AND CEA IMMUNOASSAY

[76] Inventors: Frederick J. Primus, 2012 Summerhayes Ct., Lexington, Ky. 40503; Milton D. Goldenberg, 636 Lakeshore Dr., Lexington, Ky. 40502

[21] Appl. No.: 5,355

[22] Filed: Jan. 12, 1987

Related U.S. Application Data

[63] Continuation of Ser. No. 609,607, May 14, 1984, abandoned, which is a continuation of Ser. No. 459,919, Jan. 21, 1983, abandoned.

[51] Int. Cl.$^4$ ................. G01N 33/543; G01N 33/577; C07K 15/04
[52] U.S. Cl. .................... 436/518; 530/387; 435/7; 435/68; 435/70; 435/172.2; 435/240.27; 424/1.1; 424/85.8; 436/548
[58] Field of Search .................. 530/387; 435/7, 68, 435/70, 172.2, 810, 240, 241, 948; 424/1.1, 85; 436/518, 528-534, 548, 804, 808, 813, 815

[56] References Cited

U.S. PATENT DOCUMENTS

| | | | |
|---|---|---|---|
| 3,865,689 | 2/1975 | Goldenberg | 424/1.1 |
| 3,867,363 | 2/1975 | Hansen | 260/112 R |
| 3,956,258 | 5/1976 | Hansen | 260/112 R |
| 4,075,194 | 2/1978 | Sela | 260/112.5 R |
| 4,086,217 | 4/1978 | Hanson | 260/112 R |
| 4,140,753 | 2/1979 | Edgington | 424/1.1 |
| 4,145,336 | 3/1979 | Edgington | 260/112 R |
| 4,152,410 | 5/1979 | Ishii | 424/1.1 |
| 4,172,124 | 10/1979 | Koprowski | 424/85 |
| 4,180,499 | 12/1979 | Hanson | 260/112 R |
| 4,228,236 | 10/1980 | Jakstys | 435/1 |
| 4,331,647 | 5/1982 | Goldenberg | 424/1.1 |
| 4,348,376 | 9/1982 | Goldenberg | 424/1.1 |
| 4,349,528 | 9/1982 | Koprowski | 424/1.1 |
| 4,361,544 | 11/1982 | Goldenberg | 424/1.1 |
| 4,376,110 | 3/1983 | David et al. | 436/513 |
| 4,383,985 | 5/1983 | Bartorelli | 424/1.1 |

OTHER PUBLICATIONS

Wagener, C. et al., *Journal of Immunology*, vol. 130(5), pp. 2302-2307, 2308-2315 (May 1983).
Buchegger, F. et al., *Journal of Immunological Methods* vol. 49, pp. 129-139 (1982).
Buchegger, F, et al., *Immunology Letters*, vol. 5, pp. 85-91(1982).
Hedin, A. et al., *Molecular Immunology*, vol. 19, pp. 1641-1648(1982).
Rupchik, H. Z. et al., *Cancer Research*, vol. 41, pp. 3306-3310 (Sep. 1981).
Zimmerman, R. et al., *Journal of Immunological Methods*, vol. 25, pp. 311-321 (1979).
Valdes, R. et al., *Clinical Biochemistry*, vol. 15(5), pp. 241-247 (1982).
Rogers, G.T. et al. *British Journal of Cancer*, vol. 44, pp. 371-380 (1981).
Hedin, A. et al., *Internat. Journal of Cancer*, vol. 30, pp. 547-552 (1982).
Orjasaeter, H., *Scand. Acta Path. Microbiol.*, vol. 82B, pp. 387-395 (1974).
Primus, F.J. et al. *Proc. Am. Assoc. Cancer Research*, vol. 22, p. 298ff (1981).
Von Kleist, S. et al., *Proc. Natl. Acad. Sci., U.S.A.*, vol. 69, pp. 2492-2494 (1972).

*Primary Examiner*—Margaret Moskowitz

[57] ABSTRACT

Antibodies specific to specific CEA epitopes and epitopes of CEA-cross-reactive antigens are provided. Methods of use of these antibodies and purified CEA antigens and cross-reactive antigens are also provided.

9 Claims, 1 Drawing Sheet

FIG. 1

CEA-FAMILY ANTIGENS, ANTI-CEA ANTIBODIES AND CEA IMMUNOASSAY

This is a continuation of U.S. Ser. No. 609,607, filed May 14, 1984, now abandoned, which in turn is a continuation of U.S. Ser. No. 459,919, filed Jan. 21, 1983, now abandoned.

BACKGROUND OF THE INVENTION

The major problem in chemically characterizing and determining the tumor-specificity and clinical applications of carcinoembryonic antigen (CEA) has been the use of polyclonal antiserum reagents, since CEA has been shown to contain a number of antigenic sites which could only be defined and characterized to some extent by cumbersome and mostly inexact and incomplete antibody adsorption techniques. Thus, at least twelve cross-reacting antigens have been described by the use of antiserum prepared against what was claimed to be "purified CEA". However, such "purified CEA" still contained variable quantities of these cross-reactive antigen determinants. For example, anti-blood group A antiserum is able to bind CEA as well as glycopeptide fragments of CEA.

The CEA molecule may also bear determinants which are cross-reactive with the fetal sulfoglycoprotein antigen often found in the gastric juice of gastric cancer patients. Non-specific crossreacting antigen (NCA) is one of the most abundant CEA-crossreactive determinants, occurring in high quantities in digestive tumors, normal colon, normal lung, and normal spleen, as well as in certain white blood cells, e.g., granulocytes, including malignant ones.

In addition to these known crossreactive determinants of CEA, it is likely that others exist which could interfere with the specificity of assays used to detect CEA, e.g., in vitro immunoassays, in vivo radioimmunodetection and therapy and in vitro immunohistochemical detection. Therefore, the characterization and isolation of such crossreactive substances is of interest. One useful outgrowth is the production of antisera having precise immunoreactivity, e.g., specificity to an epitope found on only one antigen in a class of closely related and cross-reactive antigens, or specificity to an epitope common to two or more of such antigens. These antisera are usful in numerous clinical and laboratory settings. Epitope is defined as a single determinant of an antigen or immunogen which influences its specificity (Dictionary of Scentific and Technical Terms, McGraw-Hill, New York, 1976).

In the past, attempts to produce monospecific anti-CEA antisera employed exhaustive adsorption with normal tissue extracts or other materials but these methods were cumbersome, difficult to control, imprecise and still beset with the problem of having crossreactive immonoglobulins present in the polyclonal antiserum.

Recently, attempts have been made to overcome the foregoing problems by the use of monoclonal antibodies. However, even the few prior attempts to produce monoclonal antibodies against CEA have failed to elucidate the different species of anti-CEA monoclonal antibodies based upon a categorization of the epitopes of CEA to which they are reactive. Thus, the extent of true CEA specificity must still await a precise characterization of the epitopes found in the family of CEA antigens and/or the elucidation of epitopes found on antigens which are cross-reactive with CEA. CEA-family antigens are defined as a group of glycoprotein or protein substances that have certain physiochemical and immunological properties in common with CEA.

It is known to use both antigens and specific antibodies in immunoassays. However, such assays have been limited to the use of antigens and antibodies which often have had ill-defined epitope specificities. Accordingly, certain applications forming a part of the present invention would not have been possible heretofore. Similar limitations in the fields of immunohistochemistry, in vivo imaging and tumor therapy are overcome by virtue of the present invention.

OBJECTS OF THE INVENTION

One object of the present invention is to provide substantially monospecific antibodies to precisely defined epitopes of CEA and/or antigens cross-reactive with CEA.

Another object of the present invention is to provide purified antigens and/or antigen fragments having precisely defined epitopes and immunoreactivity.

A further object of the invention is to provide methods for detecting the presence of a particular epitope on an antigen in the CEA family.

Yet another object of the invention is to provide a method for determining the relative proportions of at least two different epitopes present on the same antigen or on two different cross-reactive antigens.

Still another object of the invention is to provide methods of diagnosis and/or differential diagnosis of pathological conditions and/or methods for precise discrimination, characterization and titration of closely related antibodies and/or antigens.

Yet a further object of the present invention is to provide methods of detection, identification, localization, characterization and staging of malignancies as well as methods of tumor therapy.

Upon further study of the specification and appended claims, further objects and advantages of this invention will become apparent to those skilled in the art.

SUMMARY OF THE INVENTION

These and other objects which will be more readily apparent upon reading of the following disclosure may be achieved by the present invention. In a composition of matter aspect, the present invention relates to substantially monospecific antibodies to at least one CEA cross-reactive determinant, e.g., substantially pure meconium antigen.

In a methodological aspect, the present invention relates to a method for detecting the presence of a particular epitope on at least one antigen wherein said epitope is present on CEA or is present on an antigen which is cross-reactive with CEA, comprising contacting said antigen with an antibody specific to said epitope. The invention further provides a method of determining the relative proportions of at least two different epitopes present on the same or different antigen, comprising the steps of contacting an analyte containing said at least two different epitopes with at least one capture antibody capable of binding the species bearing said at least two epitopes; contacting the resultant bound species with a probe comprising a probe antibody capable of binding one of said two different epitopes; and measuring the concentration of said bound probe. The invention also provides immunoassay methods, immunohistochemical methods, in vivo detection, localization and therapy methods and methods for isolation and purification of precise antibodies, antigens and antigen fragments.

DETAILED DISCUSSION

Since the discovery of CEA, the definition of this antigen has been based on the molecule fulfilling certain physicochemical, immunochemical, and even biological criteria. As originally described, CEA was restricted to fetal and malignant gastrointestinal tissue, and was a 200,000 molecular weight beta-glycoprotein, soluble in perchloric acid and having a particular amino acid and carbohydrate composition. The identification of this substance was solely dependent upon the ability of an antiserum to recognize a specific immunodominant grouping on the glycoprotein as being the same as that detected by the original anti-CEA antiserum. It has been subsequently shown that CEA exhibits extensive heterogeneity in its physicochemical and immunological properties. The characteristics of CEA have been described in "Immunodiagnosis of Cancer, Part I", Herberman et al., Eds., Marcel Bekker, Inc., New York and Basel 1979 and "Carcinoembryonic Proteins: Recent Progress", Norgaard-Pedersen and Axelsen, Eds., Blackwell Scientific Publications, London, 1978.

A major question that has permeated many investigative studies of CEA, including its clinical application, has been the specificity of the various methods used to detect this antigen. Conventional antisera raised against CEA characteristically contain antibodies that react with a group of substances closely related to CEA. Among the latter antigens, the first to be described was nonspecific crossreacting antigen, (NCA), a 60,000 molecular size glycoprotein present in normal human tissues at levels higher than CEA, especially in lung and spleen. Several other substances have been described that are most likely NCA based on their immunochemical similarities, and these include normal glycoprotein, CEA-associated protein, colonic CEA-2, colonic carcinoma antigen-III, and tumor-associated antigen. NCA and CEA can be distinguished immunologically since they express individually distinct determinants.

A second group of CEA-like antigens in meconium and adult feces was identified. The NCA-2 characterized by Burtin and associates was slightly lower in molecular size than CEA, and expressed a determinant not shared with either NCA and CEA. NCA-2 appears more closely related to CEA than NCA since, in addition to a common determinant shared among the three antigens, a second epitope is only shared between NCA-2 and CEA. The normal fecal antigen (NFA) in adult feces has been recently separated into three molecular species, all of which are immunochemically different than NCA-2, NCA, and CEA.

Clarification of the chemical, antigenic, and developmental interrelationships between CEA-like antigens in meconium and CEA was needed. Although the clinical utility of some of these antigens was unknown and it remained to be clarified whether they represent cleavage products of CEA, CEA precursor molecules, or truly different gene products, their identification with polyclonal antibodies resulted in the delineation of at least three epitopes on CEA that are unequally shared between the related antigens. See, e.g.: Burtin et al., CEA and related antigens: A study of NCA-2, In: Fishman et al., Eds., Onco-Developmental Gene Expression, pp. 609-611, Academic Press, New York, 1976; Kuroki et al., Purification and characterization of carcinoembryonic antigen-related antigens in normal adult feces, Cancer Res., 41: 713-720, 1981; and Primus et al., Antigenic relationship of carcinoembryonic, nonspecific cross-reacting, and meconium antigens, Proc. Amer. Ass. Cancer Res., 22: 298, 1981.

The immunohistochemical localization of CEA has been widely studied in a variety of epithelial malignancies using polyclonal antibodies. Since it is present to varying degrees in normal and noncancerous diseased tissue, benign tumors, and a typical epithelium of different organs, the detection of this antigen in tissue sections cannot be used to distinguish normal or benign cells from malignant ones. Most studies have not found a correlation between CEA staining of primary tumors and diease stage or prognosis, although measurement of blood antigen levels can aid in prognosis and monitoring of therapy.

Several studies have described the development of monoclonal antibodies to CEA, but their use for the immunohistochemical detection of this antigen in tissue sections has not been adequately explored. Similarly, the application of defined monoclonals against CEA-family antigens according to the present invention for in vivo imaging of cancer, adapting the methods disclosed in Goldenberg, U.S. Pat. No. 4,348,376 and U.S. patent application Ser. No. 414,729 has now been pursued, and provides certain advantages in detecting and locating certain cancer types. Similarly, such monoclonals against epitopes on CEA-family antigens are preferred reagents for cancer immunotherapeutic procedures involving single antibodies or combinations of antibodies and antibodies labeled with therapeutic doses of radioisotopes, drugs, toxins, or similar toxic agents, as well as used for neutron-capture therapy, as described in Goldenberg, U.S. Pat. No. 4,348,376, and in U.S. Pat. No. 4,331,647 for antibody fragments.

Recent efforts to improve the immunospecificity of CEA detection and measurement by in vitro immunoassays have centered to the development and comparison to conventional assays of monoclonal antibodies against CEA. However, it is anticipated that cross-reactivity with CEA-related antigens will be encountered with monoclonal antibodies to CEA, analogous to their conventional counterparts, and that the use of monoclonal antibodies against CEA-family antigens whose epitopes have not been defined adequately will severely limit this application.

Figure 1:
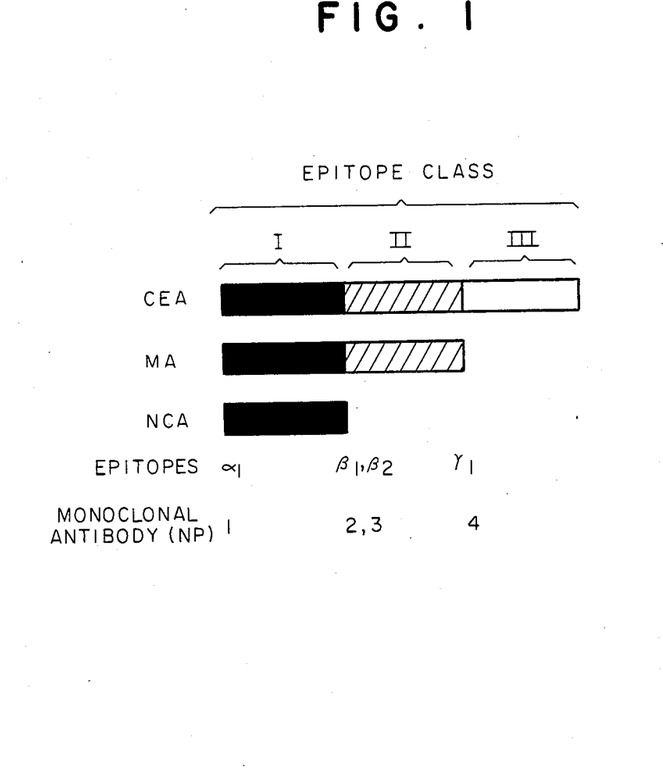

It has now been shown that monoclonal antibodies developed against colonic tumor CEA differentiate 3 general classes of antigenic determinants based on their reactivity with the CEA-like antigens, NCA and MA (FIG. 1). The smallest percentage of clones produces antibody that recognizes epitopes shared among all 3 antigens and belongs to the Class I category. Class II monoclonal antibodies react with sites shared between CEA and MA, while those of the Class III type bind only CEA, apparently recognizing determinants unique to this molecule. We have found that the affinity of the NCA cross-reactive monoclonal antibody, NP-1, for NCA was markedly lower compared to its affinity for CEA. It is possible then that the NCA cross-reactive property of a monoclonal antibody to CEA may not be revealed unless adequate quantities of antibody or NCA are used in direct labeled antigen binding or competitive inhibition assays, respectively. This does not appear to be the case for MA, since comparable quantities of NP-1 are effective in binding both CEA and MA, and MA is similar to CEA in inhibiting the reaction of NP-1 with CEA. We have shown that neutrophils stain positive with NP-1 as expected from their known synthesis of NCA but not CEA. Thus, the immunocytological staining reaction of neutrophils provides an alternative method of assessing the NCA cross-reactivity of monoclonal antibodies to CEA.

The repertoire of CEA epitopes defined by monoclonal antibodies can now be unraveled. Reciprocal blocking experiments reveal that the antibodies of Classes I and II, NP-1 and NP-2, respectively, are capable of inhibiting one another, although neither could block the Class II antibody, NP-3, or could be inhibited by NP-3. The reciprocal blocking characteristics between NP-1 and NP-2 suggest that the respective epitopes recognized by them partially overlap or are very close to one another. However, the lack of reciprocal blocking between NP-2 and NP-3 indicates that they recognize 2 separate epitopes within the Class II category. We have found, thus, that our monoclonal antibodies can differentiate at least 4 antigenic sites on colonic tumor CEA. One is shared by CEA, MA, and NCA (FIG. 1, $\alpha_1$), 2 others are shared by CEA and MA ($\beta_1$ and $\beta_2$), and a fourth appears specific for CEA ($\gamma_1$), and it is expected that additional CEA determinants will be identified within all 3 classes depicted in FIG. 1.

The NP-4 monoclonal antibody as well as the other Class III antibodies typically bind less than 50% of the CEA molecules recognized by goat antibody specific for CEA. The basis for the partial reactivity of Class III antibodies is related to discrimination of subpopulations of CEA molecules.

One major goal for the development of immunospecific monoclonal antibodies to CEA is to stimulate the evolution of refined applications of CEA detection. If various immunological forms of CEA are produced by different individuals or during different disease stages, the ultimate utility of this approach might depend on the creation of a composite of monoclonal antibodies with defined specificities. The incorporation of CEA-related antigens for the determination of monoclonal antibody epitope specificity should facilitate delineation of those antibodies having diagnostic and prognostic relevance for CEA detection. This would be further strengthened by resolving the biological interrelationships between NCA-2, or MA and CEA and the role of the former antigens as tumor markers. Finally, the use of other methods such as immunohistochemistry for the study of monoclonal antibodies to CEA can reveal molecular determinants having prognostic potential that would otherwise be unnoticed.

The disclosure herein of the present invention includes the complete disclosures of three articles by the present inventors, Primus et al., in *Cancer Research*, 43, (Feb. 1983 issue, in press).

Identification of NCA-unrelated, CEA Cross-reactive Antigens in Meconium

When NCA-neutralized anti-CEA antiserum is tested in double immunodiffusion against individual meconium samples, about an equal number of specimens give one or two precipitin bands that usually form very close to each other. In most specimens in which two bands are present, both form a reaction of partial identity with CEA while in less than 10% of unextracted or PCA-extracted specimens, the second band gives a reaction of identity with CEA. The two CEA cross-reactive precipitin bands do not coalesce with NCA which is also present in meconium. These gel diffusion patterns demonstrate the presence of two additional antibody specificities in the NCA-neutralized antiserum that recognization two common determinants on CEA unrelated to the CEA-NCA shared epitope.

In order to determine whether the NCA-unrelated, CEA cross-reactive antibodies in the CEA antiserum contributed to the measurement of CEA in meconium by radioimmunoassay (RIA), the NCA-neutralized antiserum is further absorbed with meconium samples that do not give a reaction of identity with CEA in double diffusion. This meconium-absorbed antiserum retains precipitating activity against CEA and its maximum binding of labeled CEA decreases about 10% as compared to that of the unadsorbed antiserum. However, over 80% of the antibody activity initially present in the NCA-neutralized antiserum is removed by absorption with meconium. A comparison has been made of CEA levels in meconium by RIA using Roche kit CEA antibody, NCA-neutralized antiserum, or specific anti-CEA antiserum with CEA as both the labeled tracer and inhibitor. All three antisera were adjusted in concentration to yield the same sensitivity to inhibition by CEA. Analysis of 12 meconium samples revealed that the CEA content as measured with the Roche and NCA-neutralized antisera was 3- to 10-fold greater (p<0.001; Student's t-test) than that obtained with the specific anti-CEA antiserum (Table 1).

Purification of MA from meconium

At various steps during the purification of MA, antigenic activity was monitored by RIA using Roche kit antibody, assumed to measure mainly NCA-unrelated, CEA cross-reactive substances in meconium, and by the specific anti-CEA antiserum, in order to follow CEA activity. These antigenic activities, as well as specific NCA levels at various stages in the isolation procedure, are shown in Table 2. Extraction of meconium at pH 8.0 into 40% ethanol yielded about 75% of the initial MA activity in the ethanolic supernatant. Although a large precipitate formed with ethanol fractionation, the supernatant remained viscous and highly pigmented. Chromatography of the ethanolic extract on DEAE-cellulose removed the majority of the pigment but resulted in a sub-fractionation of the MA activity throughout the entire chromatogram.

Following chromatography of the 0.1M NaCl fraction over Sephacryl S-300, the appearance of the MA activity overlapped at a slightly smaller size the elution of the radiolabeled CEA marker. The MA appearing between 225 and 270 ml elution volume was pooled and subjected to two affinity chromatography steps. The first involved passage over an immunoadsorbent containing specific anti-CEA antibody to remove the small amount of CEA

TABLE 1

Comparison of CEA Equivalents in Meconium by RIA using Commercial and Antigen-neutralized Antisera

| Sample No.[a] | Antiserum | | | |
|---|---|---|---|---|
| | CEA | | | |
| | Roche | NCA-neutralized | Specific Anti-CEA | NCA[b] |
| 1. | 140c | 180 | 15 | 94 |
| 2. | 144 | 188 | 39 | 88 |
| 3. | 196 | 244 | 73 | 109 |
| 4. | 260 | 328 | 56 | 106 |
| 5. | 102 | 138 | 13 | 78 |
| 6. | 62 | 66 | 10 | 58 |
| 7. | 140 | 59 | 29 | 91 |
| 8. | 76 | 94 | 18 | 70 |
| 9. | 136 | 176 | 35 | 96 |

TABLE 1-continued

Comparison of CEA Equivalents in Meconium by RIA using Commercial and Antigen-neutralized Antisera

| Sample No.[a] | Antiserum | | | NCA[b] |
|---|---|---|---|---|
| | CEA | | | |
| | Roche | NCA-neutralized | Specific Anti-CEA | |
| 10. | 176 | 228 | 54 | 99 |
| 11. | 33 | 45 | 7 | 41 |
| 12. | 27 | 34 | 8 | 57 |
| Mean ± S.E. | 124.3 ± 19.8 | 148.3 ± 26.5 | 20.8 ± 6.3 | 82.2 ± 6.2 |

[a]Unextracted meconium samples were initially resuspended 1:4 (w/v) in PBS and then diluted in 0.05 M borate buffer, pH 8.5, prior to assay.
[b]Values given are specific levels of NCA measured in NCA RIA.
[c]μg/g

TABLE 2

Comparative Distribution and Recovery of NCA, CEA, and MA during MA Purification from Meconium

| Isolation Step | Amount of Antigen (mg)[a] | | |
|---|---|---|---|
| | NCA | CEA | MA |
| Starting meconium | 6.5 | 0.6 | 14.5 |
| Ethanolic supernatant | 3.6 | 0.3 | 11.0 |
| DEAE, 0.1 M NaCl | 0.2 | 0.3 | 3.0 |
| S-300 | 0.02 | 0.2 | 1.5 |
| Affinity Chromatography | | | |
| Goat specific anti-CEA (unadsorbed fraction) | 0.006 | 0.01 | 0.8 |
| Monoclonal CEA antibody, NP-3 (adsorbed fraction) | 0.005 | 0.004 | 0.6 |

[a]Determined in RIA using NCA specific assay for NCA and CEA RIA using goat specific anti-CEA antiserum for CEA or Roche kit antibody for MA.

remaining associated with the MA. Although this procedure removed 95% of the CEA, 45% of the MA was lost and was not found in the adsorbed fraction (Table 2). For the second step, an immunoadsorbent containing a murine monoclonal CEA antibody, NP-3, cross-reactive with at least one group of NCA-unrelated, CEA cross-reactive substances in meconium, was used to select and purify further the MLA. Over 80% of the applied MA activity was retained by this immunoadsorbent. Overall recovery of MA activity starting with 50 g meconium was 4%, or 20% of that present in the 0.1M NaCl DEAE fraction.

Immunological Analysis of Purified MA

On the basis of neutralizing activity in RIA, the finally purified MA contained less than 1.0% CEA or NCA (Table 2). Double immunodiffusion of the MA against NCA-neutralized anti-CEA antiserum gave a single precipitin band that formed a reaction of partial identity with CEA. The two bands appearing between unextracted meconium and the latter antiserum both fused with the single line formed by purified MA. The appearance of only a single precipitin band with the purified MA suggests that it did not contain the second NCA-unrelated, CEA-related antigen. The purified MA failed to react in double diffusion with specific anti-CEA antiserum although this antiserum retained its ability to precipitate CEA. The MA also gave a single precipitin band against NCA-neutralized CEA antiserum in immunoelectrophoresis, migrating as an alpha globulin relative to serum proteins.

The antibody binding characteristics of radiolabeled MA was evaluated in RIA. As depicted in Table 3, both the Roche kit CEA antibody and the monoclonal CEA anti-

TABLE 3

Comparative Binding Activities of Radiolabeled NCA, CEA, and MA To Goat and Monoclonal Antibodies

| Antibody | Maximum Percent of Labeled Antigen Bound[a] | | |
|---|---|---|---|
| | NCA | CEA | MA |
| Goat specific anti-CEA | 0 | 62 | 8 |
| Roche kit | 6 | 69 | 63 |
| Monoclonal anti-CEA (NP-3) | 0 | 66 | 66 |
| Goat anti-NCA | 67 | 0 | 0 |

[a]Determined in antibody excess after incubation for 4 hr at 45° C. Solid-phase goat anti-mouse IgG or donkey anti-goat IgG was used to separate bound from free antigen.

body, NP-3, bound similar amounts of MA, comparable to the binding of labeled CEA by these antibodies. Over 80% of the MA was immunoreactive when tested shortly after labeling. Goat specific anti-CEA antiserum was only marginally immunoreactive with the labeled MA while goat anti-NCA antibody was unreactive. The former antiserum and Roche kit CEA antibody were similar in their reactivity with labeled CEA. Combining an excess of the specific anti-CEA and Roche kit antibodies together did not increase the maximum binding of CEA beyond that of the Roche kit CEA antibody by itself, demonstrating that the same major population of labeled CEA molecules was recognized by both antisera. Since inhibition assays and double diffusion did not reveal significant quantities of CEA in the MA, the low level of labeled MA binding to the goat specific anti-CEA antiserum was most likely due to the presence of residual cross-reactive antibody in this antiserum rather than reactivity with a labeled CEA contaminant.

Molecular Size of MA

Chromatography of the labeled MA over Sephacryl S-300 equilibrated in phosphate-buffered saline gave a single, symmetrical peak eluting at only a slightly greater elution volume than that of CEA. This relationship in the elution patterns of MA and CEA was maintained following passage over Sephacryl S-300 equilibrated and eluted with 6.0M guanidine HCl. The overlap in size distribution between MA and CEA was also observed following SDS-PAGE electrophoresis of reduced samples on calibrated gels. Estimation of the molecular size for MA by interpolation from the log molecular size plot versus migration of standards gave a value of 185,000 as compared to 200,000 for CEA. Staining of reduced MA in SDS-PAGE gels with Coomassie Brilliant Blue or periodic acid-Schiff reagent showed a single diffuse band migrating in a similar position as CEA.

Binding of MA to Concanavalin-A

The binding of radiolabeled MA to concanavalin-A Sepharose was compared to that of CEA and NCA. Over 90% of both CEA and NCA bound to this lectin while less than 20% of the MA was reactive.

Pronase Digestion of CEA and MA

Digestion of CEA with Pronase E completely abolished its reactivity with goat specific anti-CEA antiserum and resulted in a 50% decrease in its binding to the NP-3 monoclonal antibody or Roche kit goat antibody. This loss or decrease in antibody binding activity was not observed following similar treatment in the absence of enzyme. Chromatography of the enzyme digest on Sephacryl S-300 equilibrated in 6.0M guanidine HCl showed that the majority of the CEA was broken down into small fragments. By contrast, enzyme digestion of MA reduced its binding to the NP-3 and Roche kit antibodies by 20% and resulted in only a slight decrease in its molecular size.

Our isolation procedure for one of the NCA-unrelated, CEA-related molecular species in meconium, designated meconium antigen, MA, avoids application of an immunoseparation step at an early stage. This is due to our failure to find perchloric acid, PCA, solubilization alone, or in combination with alcohol as a means to provide an extract with characteristics favorable for affinity chromatography. Among the different alcohol concentrations and pH ranges tested, 40% alcohol at pH 8.5 yielded the best solubilization of MA and maximum precipitation of irrelevant protein. Subsequent chromatography on DEAWE-cellulose had the desirable feature of retaining most of the pigment while the bulk or irrelevant protein and NCA were not adsorbed. These advantages outweighed the subfractionation of MA activity observed on the ion exchanger. In the final stages, the MA was specifically adsorbed to an immunoadsorbent containing a cross-reactive monoclonal antibody to CEA, NP-3. The use of a monoclonal antibody has the advantage of selecting a molecular species homogeneous in the expression of the epitope recognized by the antibody, although differences may exist with respect to other determinants.

MA is distinct from NCA-2 and the NFA family of CEA-like antigens in adult feces, particularly NFA-2. NCA-2 and NFA-2 are similar to CEA in molecular size as well as carbohydrate and amino acid composition. Immunologically, NCA-2 shares 2 epitopes with CEA, while 3 cross-reactive sites have been demonstrated on NFA-2. We have found with monoclonal antibodies to CEA that MA, which represents one of the 2 NCA-unrelated, CEA-cross-reactive substances in meconium, shares at least 3 epitopes with CEA. The second CEA related antigen in meconium is deficient in at least one cross-reactive site that is present on both CEA and MA.

MA can be differentiated from other CEA-related antigens in meconium described previously. MA has a similar molecular size as that of CEA but is antigenically different in that it lacks at least one determinant distinguished on CEA by the conventional antiserum used by use, and this difference is also noted with monoclonal antibodies to CEA. Furthermore, MA has a much lower affinity for concanavalin A than either CEA or NCA. The low affinity of MA for this lectin does provide another possible method, one not requiring specific immunoadsorbents, for the separation of MA from CEA and NCA. Our observation that MA and the other NCA-unrelated, CEA-related antigen together appear at about a 6-fold-higher concentration than CEA in meconium may indicate that these antigens are earlier markers of differentiation than CEA. The availability of purified MA has facilitated the delineation of epitope specificity of monoclonal antibodies to CEA and the distribution of these epitopes among CEA, MA, and NCA.

Staining of Normal Colonic-Mucosa

The staining of morphologically normal colonic mucosa could be visualized with all four monoclonal antibodies. This was best observed in specimens fixed in ethanol-acetic acid (EA) rather than formalin. Positive staining of normal and tumor epithelium did not appear in control sections including those reacted with antigen-neutralized polyclonal antisera and ascites fluid. Specimens fixed in EA but not formalin frequently did show variable nonspecific staining of connective tissue in both test and control sections.

The staining of normal mucosa with the goat antisera and the monoclonal antibodies, NP-1, NP-2 and NP-4 showed that positive staining was localized mainly to the cytoplasm of columnar cells lining the upper levels of the crypts and the mucosa surface. Secretory material within the glandular or gut lumen also stained, whereas the mucus of goblet cells was antigen-negative. The intensity and presence of a staining reaction with any of the antibodies was quite variable between crypts, but was most pronounced with the goat anti-CEA and -NCA antisera, and the NP-1 monoclonal antibody. The NP-4 monoclonal antibody invariably gave a weak staining reaction that was much less apparent than that of any of other antibodies.

Besides the staining of normal colonic epithelial cells, the class I monoclonal antibody, NP-1, known to cross-react with NCA on the basis of labeled antigen binding, also stained neutrophils within blood vessels and in the extravascular tissue. This staining reaction was readily apparent in specimens fixed in EA but not formalin. Although neutrophil localization could be visualized with the immunoperoxidase procedure, it was easily discriminated with the immunoglucose oxidase method in which blocking of endogeneous peroxidase activity in neutrophils was not required, thus facilitating recognition of positive antigen staining over background levels. In addition to NP-1, only the goat anti-NCA antiserum stained neutrophils among the other antibodies studied.

Staining of Colonic Tumors.

The goat anti-CEA and -NCA antisera, and the NP-1, -2, and -3 monoclonal antibodies stained all 22 cases of moderately differentiated colonic adenocarcinomas, irrespective of their site of origin in the colon. About 70% (15/22) of these colonic adenocarcinomas gave a positive staining reaction with the class III monoclonal antibody, NP-4. The predominant staining pattern obtained in specimens fixed in formalin was a labeling of the apical surfaces of tumor cells and of intraglandular deposits (FIGS. 2 and 4). With the exception of the NP-4 antibody, the same areas of the tumor specimens were generally stained to a similar intensity with the other antibodies although an absolute correspondence was not established in cellular localization. Of the monoclonal antibodies, the NP-1 did give consistently stronger staining, both in its intensity and extent, even greater than that obtained with either goat anti-CEA or -NCA antisera in several cases. The intensity of the NP-4 staining was slightly lower in 6 cases than obtained with the other antibodies, whereas it was noticeably reduced in the remaining 9 specimens. Most of the tumor glands stained with NP-4 cases whereas 30 to 50% of the tumor tissue reacted with this antibody in the 3 other specimens. In all of these cases, over 80% of the tumor tissue reacted with the other antibodies. Two cases which classified as NP-4-negative gave a weak focal reaction in less than 10% of the tumor glands.

For 6 specimens of primary tumor, sufficient material was available for alternative fixation in EA. The intensity of staining by all the antibodies was enhanced in EA-fixed specimens over that observed following formalin fixation for each case. Cytoplasmic staining of tumor cells was very evident in EA-fixed specimens whereas following formalin fixation, it was either absent or tended to be weak. Although the increase in cytoplasmic staining in EA-fixed tissue was not as great with the NP-4 antibody compared to that of the goat antiserum, the overall staining reaction obtained with the former antibody was appreciably greater in the EA-fixed tissue as compared to the formalin-fixed specimen.

other node and the liver metastasis failed to stain with the goat anti-CEA antiserum and the NP-3 and NP-4 monoclonal antibodies. By contrast, the remaining 4 nodes and the liver metastasis were NCA-positive. When these specimens from patient D-3 were tested against the NCA cross-reactive monoclonal antibody, NP-1, the staining pattern was identical to that obtained with the goat anti-NCA antibody

TABLE 4

IMMUNOPEROXIDASE LOCALIZATION OF CEA DETERMINANTS IN METASTASES OF MODERATELY DIFFERENTIATED COLONIC TUMORS

| Patient | NP-4 Positivity of Primary Tumor[a] (%) | Metastatic Site | ANTIGEN POSITIVITY IN METASTASES | | | |
|---|---|---|---|---|---|---|
| | | | GOAT ANTISERA | | MONOCLONAL ANTIBODIES | |
| | | | CEA | NCA | NP-3 | NP-4 |
| C-2[b] | 90 | 3 nodes | | | | |
| | | a | + | + | + | Negative |
| | | b | Negative | Negative | Negative | Negative |
| | | c | Negative | Negative | Negative | Negative |
| C-3 | 90 | 1 node | + | + | + | Negative |
| D-1 | 90 | 3 nodes | + | + | + | Negative |
| | | Liver | + | + | + | Negative |
| D-3 | 80 | 5 nodes | | | | |
| | | a | + | + | + | + |
| | | b | + | + | + | + |
| | | c | + | + | + | + |
| | | d | Negative | + | Negative | Negative |
| | | e | Negative | Negative | Negative | Negative |
| D-6 | 50 | 1 node | + | + | + | Negative |
| | | Liver | + | + | + | Negative |
| D-7 | 30 | 5 nodes | + | + | + | Negative |
| D-4 | Negative | Liver | + | + | + | Negative |
| D-9 | Negative | Liver | + | + | + | Negative |
| Total positivity of metastases | | Lymph node | 14:18[c] | 15:18 | 14:18 | 3:18 |
| | | Liver | 4:5 | 5:5 | 4:5 | 0:5 |

[a]Percentage of primary tumor glands staining positive with NP-4
[b]Letter designates Dukes' stage; the number specifically identifies individual patients
[c]Ratio of number positive in total number tested Only one case of anaplastic carcinoma was studied and this was completely negative with all the goat and monoclonal antibodies.

NP-4 Staining of Metastases.

Of the 22 cases of moderately differentiated adenocarcinomas examined, 1/1, 5/7, ¾, and 6/10 of the primary tumors from Dukes' stage A, B, C, and D patients, respectively, reacted with NP-4. Although the number of patients is too few to arrive at a precise correlation NP-4 reactivity and clinical staging, these preliminary results suggest that an absolute relationship will not be established. A relationship was also not apparent between NP-4 reactivity and the location of the tumor in the colon or rectum.

Regional lymph node and/or liver metastases were available for study as formalin-fixed specimens from 8 of the above patients, 2 and 6 cases from Dukes' C and D stage, respectively. These specimens were stained with the goat anti-CEA and -NCA antibodies, and the NP-3 and NP-4 monoclonal antibodies (Table 4). The NP-4 antibody gave only a few positive staining reactions in metastatic tumors even in patients who had over 80% of their primary tumor tissue, as visualized in single sections, staining positive with this antibody. The majority of these metastases did retain reactivity with the goat antibodies and the NP-3 monoclonal antibody.

The regional lymph node and/or liver metastases of two patients, C-2 and D-3, showed further differences in their stanning phenotype (Table 4). Two of the nodes from patient C-2 were unreactive with all the antibodies while the third node gave a negative reaction with only the NP-4 antibody. One node from patient D-3 was not stained by any of the antibodies and, in addition, an- The possibility that the eventual aggressive behavior of morphologically similar tumors can be ascertained by the detection of certain antigenic markers they elaborate has emerged from immunohistochemical studies of some cancer types,. With other markers, the discrimination of molecular or suble determinant changes of an antigen might be missed due to the diversity of epitopes inherently recognized by polyclonal antibodies. The identification of these molecular changes would be significant if they are indeed linked to a concomitant alteration in the biological expression of the cancer cell. The precise immunospecificity of monoclonal antibodies provides a tool by which one can probe for these antigenic modifications and, in the study described herein, we have compared the staining characteristics of colonic adenocarcinomas using a polyclonal goat antibody and four monoclonal antibodies derived against CEA.

As expected from our previous studies, which demonstrated by immunohistochemistry with conventional antisera the presence of CEA in normal colon, this tissue was stained by the three cross-reactive monoclonal antibodies. This was also true for the NP-4 antibody which lacks cross-reactivity with NCA and MA but appears to recognize a subpopulation of CEA molecules based on labeled antigen binding. The staining by these antibodies appeared to be localized within the same cell as visualized in separate tissue sections reacted with individual antibodies. Like the conventional antserum used in this study but unlike those of some other investigators (Huitric et al., Lab. Invest., 34:97–107, 1976), the monoclonal antibodies failed to stain the mucus of colonic goblet cells. Of the monoclonal antibodies, it was also found that only NP-1 stained neutrophils which likewise reacted with goat anti-NCA antibody, as predicted by the known synthesis of NCA by these cells. Thus, immunohistochemical procedures can both confirm the specificity of monoclonal antibodies to CEA determined by other methods, and be useful in identifying their NCA cross-reactivity when other methods are not readily available.

With the exception of the NP-4 antibody, the other monoclonal antibodies and the conventional goat antisera stained all of the primary moderately differentiated colonic tumors and most of the regional lymph node and liver metastases examined in this study. A different staining pattern emerged with NP-4 in that about 30% of the primary tumors were unreactive, and most of the metastases arising from NP-4-positive primary tumors did not stain with this antibody. This does not mean that the molecule or determinant recognized by NP-4 is universally deleted from metastatic tumor cells. We have found that the staining intensity obtained with the NP-4 monoclonal antibody was considerably improved in primary tumor specimens fixed in EA rather than formalin. Alternatively, the almost virtual absence of NP-4 staining of metastases in patients with positive primary tumors may suggest a quantitative, if not qualitative, deletion in the expression of its recognized determinant or antigen from metastatic tumor cells, or the cloning of antigen-negative tumor cells.

Although we have not as yet compared determinant expression in tissues with that in the circulation, the existence of tissular CEA determinant heterogeneity indicates that potential problems will arise in the correlation between blood levels of this antigen, measured with monoclonal antibodies, and disease activity.

On the basis of the immunohistochemical studies presented here, however, we would anticipate divergent assay results and a poor correlatiion with disease activity, depending upon the relative contribution to circulating antigen by tumor in different locations and the specificity of the monoclonal antibody used in the immunoassay.

While fundamental questions remain to be answered with regard to antibody specificity and the presence of reactive antigen in the tissue and blood, it is clear that immunohistochemistry, which can be conveniently applied to conventional histopathology specimens, will have a major role in distinguishing monoclonal antibodies reactive with CEA variants or determinants that have prognostic and diagnostic value. This also applies to the appropriate selection of monoclonal antibodies for radioimmunodetection and antibody-directed therapy of colonic tumors.

Classes of CEA Hybridoma Clones

Antigen binding profiles revealed that CEA hybridoma clones could be differentiated into 3 distinct classes based on their comparative immunoreactivity with CEA, MA, and NCA (Table 5). Most of the clones from the first fusion produced antibody that bound both CEA and MA (Class II), while the clones from the second fusion about equally distributed between Class II and those showing CEA reactivity only (Class III). Reactivity with all 3 antigens (Class I) was found in 16 and 2% of the clones from the first and second fusions, respectively. The results depicted in Table 5 were obtained by assaying 50 -ul aliquots of undiluted culture supernatants. The percentage of binding of labeled CEA by clones of Classes I and II was similar, whereas Class III clones consistently gave lower values. Although the reactivity of clones of Classes I and II with MA was similar to their binding of CEA, culture supernatants of Class I clones averaged only 9.9% (±2.4 S.E.) binding of labeled NCA. The lower binding of NCA is attributed to the requirements for higher levels of antibody in order to obtain elevated NCA binding as compared to the amount of antibody needed for CEA and MA binding. Optimal binding of NCA also required a longer incubation time as compared to that for CEA and MA.

None of the CEA-reactive cultures bound to human erythrocytes from both secretor and nonsecretor individuals.

Antigen Binding in RIA of Selected Clones

Four hybridoma clones, one from Class I (NP-1), 2 from Class II (NP-2 and NP-3), and one from Class III

TABLE 5

Comparative RIA of Hybridoma Culture Supernatants Containing CEA Antibody with CEA, MA, and NCA[a].

| FUSION NUMBER | Labeled Antigen Reactivity | | |
|---|---|---|---|
| | CEA, MA, and NCA | CEA and MA | CEA only |
| 1. | 6/37[b](16) | 26/37 (73) | 5/37 (14) |
| 2. | 1/50 (2) | 27/50 (54) | 22/50 (44) |
| Total | 7/87 (8) | 53/87 (61) | 27/87 (31) |
| Percent CEA Binding[c] | 37.0 ± 9.6 | 37.7 ± 2.4 | 20.4 ± 1.7 |
| Class Designation | I | II | III |

[a]Hybridoma culture supernatants, 50 μl, were individually assayed for binding to the radiolabeled antigens.
[b]The number of clones belonging to a specified class over the total number of clones demonstrating anti-CEA activity. Number in parentheses indicates the percentage of clones belonging to each class.
[c]Mean ± S.E.

(NP-4) were selected and recloned for further characterization. The NP-1, -2, and -3 antibodies were purified from culture medium containing agamma horse serum, whereas NP-4 was used as an ascites fluid. NP-1, -2, and -3 clones produced antibodies of the IgG1 (κ) subclass, while the NP-4 clone produced antibody of the IgG1 (λ) isotype. These 4 monoclonal antibodies failed to precipitate CEA in double immunodiffusion. NP-1, -2, and -3 bound 60 to 70% of CEA and MA, similar to the immunoreactivity of goat anti-CEA antibody with these antigens. NP-4 failed to bind MA and maximally bound only about 30% of the radiolabeled CEA. Normal murine ascites fluid or serum did not react with CEA, and the maximum CEA binding level observed with NP-4 was characteristic of the other Class III hybridomas. In addition to binding CEA and MA, the Class I monoclonal antibody, NP-1, reacted with labeled NCA to the same extent as goat anti-NCA antibody. However, 2600 ng of NP-1 were required to bind 30% of the labeled NCA, whereas only 1.1 and 2.5 ng of this antibody were needed to bind the same level of CEA and MA, respectively. Slightly higher quantities of NP-2 were required to bind MA as compared to CEA, while the reverse was true for NP-3.

Since the Class III hybridoma clone, NP-4, maximally bound only 30% of the labeled CEA as contrasted to 70% binding by goat anti-CEA antibody, 2 -experiments were designed to show that NP-4 was recognizing a population of CEA molecules also detected by goat antibody. The first experiment tested for additive binding of CEA mixing NP-4 and goat antiserum together, in quantities at maximal antigen binding level for each, incubating, and then separating bound from free antigen with Z-gel. The results of this test showed that the binding of CEA by the combined antibody mixture was no greater than that obtained with goat antiserum alone. If NP-4 were recognizing a population of labeled molecules distinct from those reacted with by goat antiserum, then a mixture of the 2 antibodies should have yielded an antigen binding percentage approximating a summation of the individual binding percentages. The second experiment evaluated the ability of goat antibody to block the reaction of NP-4 with the labeled antigen by sequential incubation of the antigen with goat antibody followed by NP-4, then separating bound from free antigen with solid-phase goat anti-mouse antibody. As expected on the basis of the additive experiment, the goat anti-CEA antiserum completely inhibited the binding of NP-4 to the labeled antigen. Normal goat serum or irrelevant goat antibody against NCA was without effect.

Competitive Inhibition and Antibody Affinity

The ability of unlabeled CEA to inhibit the reaction of the 4 hybridoma monoclonal antibodies with labeled CEA was tested in competitive RIA. In this procedure, the quantity of monoclonal or goat antibody used was adjusted to give 50% binding of labeled antigen in the absence of unlabeled antigen. Under these conditions, the 4 monoclonal antibodies generated markedly different antigen inhibition curves. The NP-1 antibody was similar to Roche kit goat antibody in sensitivity to antigen inhibition, whereas the NP-2, -3, and -4 monoclonal for inhibition. Using $M_r$ 200,000 as the molecular size for CEA, the data obtained were transformed into the determination of average affinity constants by the method of Mueller (Table 6). The K values obtained by this treatment, as well as the ng of CEA per

TABLE 6

Affinity Constants of Monoclonal Antibodies Against CEA. The average affinity constant of Roche kit antibody and monoclonal antibodies was determined in competitive CEA RIA (21).

| Antibody | CEA[a] | | |
|---|---|---|---|
| | $[I_t](M)$ | ng/ml | $K (M^{-1})$ |
| Goat | $3.5 \times 10^{-12}$ | 0.63 | $1.6 \times 10^{12}$ |
| NP-1 | $6.6 \times 10^{-12}$ | 1.2 | $5.3 \times 10^{11}$ |
| NP-2 | $4.3 \times 10^{-11}$ | 7.8 | $1.9 \times 10^{11}$ |
| NP-3 | $6.0 \times 10^{-10}$ | 108 | $4.5 \times 10^{9}$ |
| NP-4 | $3.0 \times 10^{-9}$ | 540 | $8.9 \times 10^{8}$ |

[a]The molar concentration or ng/ml of unlabeled CEA required to inhibit by 50% antibody binding of labeled CEA.

ml needed to inhibit binding by 50%, further illustrate the similarity in antibody affinity between NP-1 and goat anti-CEA antibody and the decreasing antibody affinity of NP-2, -3, and -4.

Since markedly higher levels of the NP-1 monoclonal antibody were required to bind labeled NCA than those needed for labeled CEA or MA, a comparison was made among the abilities of CEA, MA, and NCA to inhibit the reaction of NP-1 with labeled CEA. The results demonstrate that both MA and NCA can compete in this reaction, but, compared to CEA, it required about 2 and 8 times more MA and NCA, respectively, to depress binding by 50%. The inhibition by MA and NCA was not due to CEa contamination, since these preparations contained less than 1.0% CEA as determined in RIA with goat specific anti-CEA antibody. Only at the highest concentrations of NCA tested would the CEA contaminant begin to contribute to the inhibition induced by NCA. Using molecular weights of 200,000, 185,000, and 60,000 for CEA, MA, and NCA, respectively, the affinity of NP-1 was slightly lower for MA and 10 times lower for NCA compared to its affinity for CEA.

Blocking of Monoclonal Antibody Binding

The 2 monoclonal antibodies, NP-2 and NP-3, were initially selected for study on the basis of incubation buffer ionic strength influence on CEA binding. It was found that appreciably greater quantities of goat, NP-1, and NP-2 antibodies are needed to obtain 30% binding of labeled CEA in 0.1M compared to 0.01M ammonium acetate, being 36 times greater for NP-2. By contrast, antigen binding by NP-3 and NP-4 in these 2 buffers was very similar. The possibility that NP-2 and NP-3 recognize separate epitopes within the Class II category was analyzed by reciprocal blocking experiments. In these studies, solid-phase polyclonal goat anti-CEA, sensitized with CEA, was used in a sandwich system with radiolabeled monoclonal antibody probes. The ability of unlabeled monoclonal antibodies to inhibit the binding of radiolabeled antibodies was evaluated in reciprocal cross-blocking experiments. Although belonging to separate class categories, NP-1 and NP-2 were very efficient in blocking one another. NP-3 could not block NP-1 and NP-2 binding at the highest concentrations tested, nor could the latter monoclonal antibodies inhibit the binding of NP-3 to CEA.

The present invention includes a general method for immunoassay whereby the relative proportions of at least two different epitopes present on the same or different antigen may be determined. The method comprises the steps of:

(a) contacting an analyte containing at least two different epitopes, on the same molecule or on different molecules, with at least one capture antibody capable of binding the species bearing these two epitopes;

(b) contacting the resultant bound species with a probe comprising a probe antibody capable of binding one of the two different epitopes; and (c) measuring the concentration of the bound probe.

The capture antibody will be an antibody or antibody mixture which is bound, capable of being bound, or capable of being precipitated to form a solid phase and-/or which can be separated from the analyte by any means. For example, the capture antibody may be a polyclonal antibody capable of binding two different antigens containing the two different epitopes, a polyclonal or monoclonal or substantially monospecific antibody specific to an epitope common to two different antigens bearing the two different epitopes to be determined, an antibody capable of binding to an epitope which is different from both of the two epitopes to be determined but which is on the same antigen as those two different epitopes, or any other equivalent antibody or antibody mixture, including antibody fragments having appropriate specificity. The capture antibody may be bound to a solid support, e.g., solid particles of various materials, e.g., polystyrene, polyethylene, glass and the like, or may be capable of being bound at a later time to form a separable phase, e.g., by reaction with another antibody specific to the capture antibody, by precipitation or the like. Alternatively, the capture antibody may be bound to a material capable of being separated by, e.g., magnetization or other known process.

Once the species bearing the two epitopes to be determined is/are bound to the capture antibody, the resultant bound species is/are contacted with a probe antibody capable of binding one of the two different epitopes but not the other. Preferably, the probe antibody will be a substantially monospecific and/or monoclonal antibody. Binding of the probe antibody permits differentiation between the capture antibody-bound epitopes. This determination can be made using a variety of techniques adapted from conventional immunoassay procedures. Suitable such techniques include attaching a label to the probe antibody, e.g., a radioisotope, a fluorescent marker, an enzyme and the like, separating the complex including the capture antibody, the species containing the two epitopes to be determined and the probe antibody from the remainder of the analyte, and measuring the concentration of the label. Alternatively, competitive inhibition and/or other indirect measurements can be made. It will be appreciated that precisely defined antigens and/or antigen fragments, including antigen fragments having few or, preferably, a single epitope thereon, can be used as the capture species to detect antibodies by immunoassay, using further probe species adapted to such procedures.

Immunosassays based on detection of an antigen in a liquid specimen in vitro are generally divided into competitive and non-competitive procedures that can use as well, either antibody or antigen linked to a solid-phase carrier. The specific type of assay chosen depends on the availability of purified antibody and antigen, the ease by which these reagents can be labeled with markers used to quantitate the reaction, the level of desired sensitivity, the intended purpose of the assay, and the assay adaptability to automation.

Solid-phase, non-competitive immunoassays using enzyme-labeled antibodies are well-suited for multiple antigen and/or epitope determination due to their simplicity and ease of execution. Two main steps are involved in this type of procedure. An antigen solution is exposed to antibody immobilized on an inert carrier. During this antigen capturing stage, the immobilized antibody reacts with antigens, after which the entire complex is separated from extraneous substances in the antigen solution by washing the inert carrier with buffer. Next, excess enzyme-labeled, free antibody is added to the immobilized antibody carrier-antigen complex. During this antibody probe stage, the free antibody interacts with antigen secondarily attached to the carrier by the capturing antibody. The carrier is then washed, incubated with enzyme substrate solution, and the amount of enzyme-labeled, antibody found is directly proportional to the concentration of antigen and/or epitopes in the test specimen.

The monoclonal antibodies identified in this invention are selected on the basis of both defined epitope specificity and elevated binding constants, as for example, a monoclonal antibody that recognizes a common CEA-MA-NCA epitope has an affinity constant of $5.3 \times 10^{11} M^{-1}$ and this is only slightly less than the $1.6 \times 10^{12} M^{-1}$ constant for polyclonal antibody. The immunoassay is constructed in two types. The first has a broad spectrum monoclonal antibody, recognizing all members of the CEA-family, as the capturing antibody attached to polystyrene balls by hydrophobic bonds. Other inert carriers such as agarose, cellulose, acrylamide, polycarbonate and iron particles can also be used. The balls are then exposed to a biological specimen such as serum or a known amount of antigen, CEA, MA, or NCA, which is used to relate binding of free antibody probes to concentration of antigen in the test specimen. After incubation and washing, individual balls with associated captured antigen are exposed to enzyme-labeled monoclonal and polyclonal antibody probes that have specific-or common-epitope recognition. Suitable marker enzymes for antibody labeling include peroxidase, glucose oxidase, alkaline phosphatase, or $\beta$-galactosidase. Alternatively, fluoroescent or radioactive compounds can be used for antibody labeling instead of enzymes. After incubation and washing, the enzyme activity bound to the balls is measured by incubation with an appropriate enzyme substrate solution and the level of colored product generated is determined spectrophotometrically. By this method, specific levels of each antigen are determined and are compared individually among patients with similar or different diseases, or are compared together as specific antigen ratios. The specific antigen levels, their aggregate ratios, and partial or total common epitope expression are expected to vary between patients having malignant versus non-malignant diseases, and during different stages of disease activity or dissemination.

The second type of solid-phase assay is constructed in an identical fashion as the first, the major exception being that monospecific monoclonal and polyclonal antibodies are separately attached to balls and are used for antigen capture. Monoclonal antibodies having specificity for a second specific epitope on the appropriate antigens, distinct from that of the capturing antibody, or common-epitope antibodies are used as antibody probes.

These immunoassay techniques may be used to detect specific antigens and/or antibodies in an analyte, to evaluate the purity and/or cross-reactivity of heterogeneous antigen and/or antibody mixtures, to determine the purity and titer of antigens and/or antibodies, including antigens or antibodies labeled with, e.g., a drug of a marker such as an enzyme, a label or a toxin, or to determine the ratio of antigens present in a mixture of closely related antigens, e.g., the CEA-family antigens, the isoenzymes in an enzyme extract, the ratio of K/L light chains of antibodies produced by lymphoma cells, the relative elevation of meconium antigen in blood or amniotic fluid, and the like.

The ability to make qualitative and/or quantitative determinations of the presence and/or relative abundance of closely related antigens and/or epitopes characteristic thereof can be useful in a variety of diagnostic situations. For example, the ratio of CEA to NCA can be used to aid in a differential diagnosis of digestive cancer, especially colorectal cancer, as opposed to non-neoplastic digestive tract diseases, e.g., ulcerative colitis. Another example is the use of the foregoing procedure to detect the presence of meconium antigen in blood as a diagnostic and/or prognostic indicator of cystic fibrosis. Elevated MA levels in amniotic fluid, and/or elevated relative proportions of MA over CEA in amniotic fluid, are indicators of fetal/maternal problems, especially fetal distress. The detection of the relative proportions of the $\alpha$-subunit and the $\beta$-subunit of human chorionic gonadotropin can aid in the diagnosis of specific types of tumors, e.g., trophoblastic tumors.

The foregoing methods can also be adapted to determining the ratios of subpopulations of circulating T-lymphocytes. This is useful for diagnosis of infectious diseases, e.g., influenza and hepatitis, and for typing of lymphoid malignancies. Use of this refinement of immunoassay for determination of the presence and/or relative proportions of isoenzymes can aid in the detection and management of a variety of pathologies characterized by abnormal levels of isoenzymes, e.g., myocardial infarction, which is characterized by release of creative kinase-MB into the bloodstream in elevated levels, and also by abnormal levels of certain liver dehydrogenase isoenzymes.

Use of immunoassay techniques and/or immunohistochemical techniques for the detection of particular tumor-associated determinants is useful in diagnosis. For example, the presence of a particular determinant will be supportive evidence of malignancy, and where a suspected malignancy is in a heterotopic site, this will be a strong indication of the presence of a metastatic tumor. Detection of metastasis of CEA-producing tumors by showing the presence of determinants characteristic of CEA but which are heterotopic, i.e., found in an organ different from the organ of origin, and in a possibly malignant cell, is strong confirming evidence of a tumor metastasis.

Progression of a tumor from early to more advanced states of malignancy can be detected by expression of certain determinants or their deletion. This can be detected by radioimmunoassay and/or immunohistochemical methods, preferably by the use of monoclonal antibodies to specific epitopes. The presence or absence of certain determinants may thus be indicative or correlate with particular stages of tumor progression, serving also as prognostic indicators.

Another example of the use of the present methods is the detection of NCA in leukemia patients, as an indicator of tumor burden in myelocytic leukemias.

The present invention permits the detection of organ-specific epitopes on CEA-family antigens using antibodies specific to these epitopes. Analogously to the above procedures, these antibodies may be used for the determination of the histogenetic origins of neoplasms by immunohistochemical, in vitro immunoassay and in vivo imaging procedures, as well as for more selective immunotherapy of such tumors. The methods of tumor localization, detection and therapy disclosed in, inter alia, U.S. Pat. Nos. 4,331,647, 4,348,376 and 4,361,544, the disclosures of each of which are incorporated herein by reference, can be combined with the methods and compositions of the present invention as indicated hereinabove. For example, monoclonal antibodies specific to particular epitopes on CEA can be used according to the method of U.S. Pat. No. 4,348,376 for tumor localization and/or therapy. Mixtures of F$_{(ab)2}$ fragments from two different antibodies specific to CEA-family antigens can be used to prepare bivalent hybrid antibody fragments for use according to the method of U.S. Pat. No. 4,331,647. Antibodies specific to precise epitopes of CEA and colon specific antigen-p (CSAp) can be used cooperatively, with appropriate radiolabels, to produce an antibody preparation having increased avidity for particular tumor types, especially colorectal cancers.

It is also useful to employ the new monoclonal antibodies of the present invention for the detection of myelocytic leukemias and certain lymphomas, either using immunohistochemical techniques or immunoassay procedures. Certain CEA-specific antibodies which are applied to CEA detection in tissue samples by immunohistochemical techniques will be comparable regardless of whether they are monoclonal antibodies or polyclonal antibodies, while in other cases, the use of monoclonal antibodies according to the present invention will have significant advantages, especially the fact that they give more consistent results. Other immunohistochemical applications of antigens according to the invention include the use of these antigens, having different labels introduced thereon, e.g., radiolabels, fluorescent labels and the like, for multiple marker localization in the same tissue specimen. Another use is for the detection of marker ratios in tissues, as in the determination of K/L light chain ratios in lymphoma phenotyping, or the detection of NCA in the tissues of leukemia patients.

The antibodies of the invention can be used for purification of antigenic determinants using conventional techniques, e.g., affinity chromatography, precipitation and the like. They can also be used as an aid to elucidation of new determinants and as yet undefined determinants in famlies of related antigens. Conversely, purified antigens, including antigen fragments containing single epitopes find application in detecting, purifying, titrating and characterizing antibodies, e.g., monoclonal antibodies, heterogeneous antibody preparations, and other preparations such as blood, tissue, other body fluids and the like. Purified antigens are of course useful for the production of highly monospecific antibodies without the necessity of fusion, i.e., production of antibodies having substantially the same monospecificity as monoclonal antibodies but without using hybridoma techniques for their production.

Digestion of highly purified antigens to form antigenic fragments can further amplify the usefulness of such techniques where the fragments are limited to a single immunologically active epitope. The antigens of the invention can be fragmented by exposure to, e.g., proteolytic enzymes such as staphylococcus protease V-8, trypsin, chymotrypsin, thermolysin and the like. Fragments can be isolated by using immunoabsorbents like containing bound monoclonal antibodies having either common or specific epitope specificity. Preferably, such fragments will only contain a single epitope.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Purification of CEA and NCA from Tumor Tissue

The preparation of CEA used in this study, other than for RIA, was isolated from liver metastases of colonic adenocarcinoma according to the procedure of Krupey et al. (Immunochem. 9: 617, 1972), as modified by Newman et al. (Cancer Res. 34: 2125, 1974). Briefly, the concentrated PCA extract was applied to a 1:1 mixture of DEAE and CM cellulose (Whatman, Clifton, N.J.) equilibrated to 0.1M NH$_4$Ac, pH 4.0. Adsorbed substances were eluted with a discontinuous gradient of 0.05M, 0.1M, and 0.2M NaCl in the same buffer. Approximately 30% of the initial CEA immunoreactivity in the PCA extract appeared in each of the application buffer, (A) 0.05M NaCl (B), and 0.1M NaCl (C) fractions as monitored with the Roche CEA assay kit (Nutley, N.J.). The C fraction was subjected to sequential chromatography over Sepharose 6B and Sephadex G-200 (Pharmacia, Piscataway, N.J.) in 0.05M PO$_4$, pH 5.0, plus 0.15M NaCl buffer. A final separation step over concanavalin-A Sepharose (Pharmacia) was performed according to the method of Pritchard and Todd (Cancer Res., 36: 4699–4701, 1976), whereby adsorbed antigen was eluted with 20% (w/v) α-methyl-D-glucoside at room temperature. The CEA was dialyzed against distilled water, lyophilized, and dried to constant weight over $CaCl_2$. The purified CEA had a specific activity (neutralizing activity per unit dry weight) of 0.7 as determined in the Roche assay. It migrated in immunoelectrophoresis as an α-globulin compared to normal human serum and gave a band of identity with Roche reference CEA in double immunodiffusion. A single band was observed in 7.5% polyacrylamide gels stained for protein or carbohydrate.

The A fraction from the DEAE-CM cellulose ion exchanger contained NCA and was separated from CEA also present in this fraction by chromatography over a 5-×90-cm Sephadex G-200 column. The presence of NCA was monitored by double immunodiffusion and a peak of antigen activity appeared at an elution volume of 1000 to 1200 ml. This fraction was subjected to concanavalin-A Sepharose chromatography, as described for CEA, and the adsorbed antigen was further purified by passage over an anti-NCA immunoadsorbent. NCA was eluted from the immunoadsorbent with 0.2M glycine-HCl, pH 2.0, neutralized with NaOH, dialyzed against PBS, and concentrated over an Amicon PM-10 membrane (Amicon, Lexington, Mass.). The purified NCA migrated as a -globulin in immunoelectrophoresis and gave a reaction of identity with reference NCA in double immunodiffusion. NCA was also partially purified from normal spleen by immunoprecipitation, as previously described (Primus et al., J. Immunol. 118: 55, 1977).

EXAMPLE 2

Purification of MA from Meconium

Meconium, 50 g. was suspended in 300 ml of 0.1M $PO_4$, pH 8.0, and mixed overnight at 4°. After centrifugation for 30 min at 10,000×g, the pH of the supernatant was adjusted to 8.5 and cold absolute ethanol was added to a final 40% concentration. The ethanolic supernatant obtained after centrifugation was dialyzed against 0.02M $PO_4$, pH 7.8, mixed with 5.0 g of DE 52 (Whatman) equilibrated with the same buffer, and poured into a 2.6-×20-cm column. Following the elution of unbound substances with the application buffer, adsorbed materials were removed with a discontinuous NaCl gradient in the same buffer. Antigenic activity emerging in the 0.1M NaCl fraction was dialyzed against 0.05M $PO_4$, pH 5.0, plus 0.15M NaCl, concentrated over a YM-10 membrane (Amicon), and applied to a 2.6-×90 cm Sephacryl S-300 (Pharmacia) column. Antigenic activity contained with the 225 to 270 ml elution volume was pooled, dialyzed against 0.1M $PO_4$, pH 7.0, and passed over an immunoadsorbent containing goat specific anti-CEA antibody. The unadsorbed fraction from the latter immunoadsorbent was then applied to a second immunoadsorbent containing a murine monoclonal CEA antibody, NP-3, described elsewhere herein. On the basis of blocking studies with cross-reactive CEA antibodies from goats, NP-3 was shown to recognize a determinant shared between CIA and NCA-unrelated, CEA-related substances in meconium. Antigen bound to the NP-3 immunoadsorbent was eluted as described above for NCA purification. The adsorbed fraction was neutralized, dialyzed against PBS, and concentrated over a YM-10 membrane.

EXAMPLE 3

Animal Immunization and Antiserum Preparation

Goat anti-CEA antiserum was prepared by the injection of 100 to 200 μg of purified CEA coupled to an equal amount of methylated bovine serum albumin (Sigma, St. Louis, Mo.) and emulsified in an equal volume of complete Freund's adjuvant (Difco, Detroit, Mich.). Incomplete adjuvant was used after the initial injection. The goat anti-CEA antiserum, obtained after 21 injections, was repeatedly absorbed with A, B, and O erythrocytes from both $Le^a$ and $Le^b$ individuals until free of hemagglutinating activity. The antiserum was then sequentially chromatographed over normal colon and NCA immunoadsorbents, the unadsorbed fraction being used in both cases. Completeness of adsorption was analyzed in double immunodiffusion against normal tissue extracts and NCA. A portion of the NCA-neutralized anti-CEA antiserum was further absorbed with meconium by adding 250 mg (dry weight) of alcohol-extracted meconium per ml of antiserum. After separation of the immune precipitate, completeness of absorption was verified in double immunodiffusion against meconium. This NCA and meconium absorbed antiserum is hereafter identifies as specific anti-CEA antiserum.

Goat anti-NCA antiserum was freed of antibodies cross-reacting with CEA by passage over a CEA immunoadsorbent. The CEA-neutralized antiserum failed to react with CEA in double immunodiffusion or RIA.

EXAMPLE 4

Antigens and Goat Antisera

CEA, used for mouse immunization, and NCA were isolated from liver metastases of a colonic adenocarcinoma, and MA was purified from meconium as described herein. All antigens were radioiodinated by the chloramine-T method with $^{125}I$ (Amersham, Arlington Heights, IL) to a specific activity of approximately 30 Ci/g. Radiolabeled CEA from the Roche CEA assay kit (Nutley, N.J.) was used routinely when it was found to give results similar to those obtained with the CEA used for immunization.

The goat anti-CEA antibody in the Roche kit was used in RIA. Goat anti-NCA antiserum (no. 80) was generously supplied by Mr. Edward Newman, Roche Research Center, Nutley N.J. and, before use, was depleted of antibodies cross-reacting with CEA by passage over a CEA immunoadsorbent.

Binding characteristics of labeled CEA, MA, and NCA with goat antisera are described herein. The Roche kit antibody and a goat anti-CEA antiserum made specific for CEA by absorption with NCA and meconium reacted similar with labeled CEA. The labeled MA was bound by Roche kit antibody but not by the goat specific anti-CEA antiserum. NCA did not react with either the Roche kit antibody or the specific anti-CEA antiserum nor did goat specific anti-NCA antibody bind CEA and MA.

EXAMPLE 5

Mouse Immunization

BALB/c female mice (Harlan-Sprague-Dawley, Indianapolis, IN.), 3 to 4 months old, were given 3 i.p.

injections of 20 μg of CEA in incomplete Freund's adjuvant. The second and third injections were separated from the first by 2 and 8 weeks, respectively. Six months after the initial immunization, two mice demonstrating serum antibody against CEA were selected as spleen cell donors and received a final series of CEA injections, 50 μg each in saline, according to the immunization protocol of Stahli et al. in Res. Monogr. Immunol. 3:201, 1981. At 4 days and 1 day prior to fusion, the CEA was injected i.p. while at 3 and 2 days before fusion, it was equally divided for both i.p. and i.v. injections.

EXAMPLE 6

Cell Fusion and Cloning

Two separate fusions were performed with spleen cells obtained from two CEA-immunized mice according to the method of McKearn, in Kennett et al., Eds. Monoclonal Antibodies Hybridomas: A New Dimenson in Biological Analyses, pp. 368–369, New York, Plenum Pub. Co., 1980. For each fusion, $5 \times 10^7$ Ficoll-Hypaque separated spleen cells and $5 \times 10^6$ P3-X63-Ag8.653 myeloma cells (Salk Institute, San Diego, CA.) were mixed in a 60 mm culture dish and centrifugal at $250 \times g$ for 5 min. Excess medium was removed and replaced with 1.0 ml of 50% (v/v) polyethylene glycol (1500, Fisher) in Dulbecco's Modified Eagle's medium (GIBCO, Grand Island, N.Y.) at 37°. After a 30-sec exposure to polyethylene glycol, the cells were washed twice and then incubated overnight in 5 ml of Dulbecco's Modified Eagle's medium supplemented with 20% agamma horse serum (KC Biologicals, Inc., Lenexa, KS), 2 mM L-glutamine, 1 mM sodium pyruvate, 0.55 mM L-arginine, 0.27 mM L-asparagine, and 14 μM folic acid. The cells were dispersed in 30 more ml of the latter medium further supplemented with 0.1 mM hypoxanthine, 0.4 μM aminopterin, and 16 μM thymidine. The cell suspension was distributed into 96-well microwell plates (Costar, Cambridge, Mass.), 100 μl per well. An additional 100 μl of medium minus the aminopterin were added to the wells 7 days later. After 2 to 4 weeks of culture, the medium from wells containing growing cell clones was assayed for CEA antibody by RIA. CEA antibody-positive wells were expanded into 24-well plates (Costar) containing $10^7$ irradiated (1400 R) Lewis rat thymocytes per well. Upon reaching confluence, all cultures remaining antibody-positive were frozen while 4 clones were twice recloned at limiting dilution. Hybridomas were recloned in 96-well plates containing $10^6$ irradiated Lewis rat thymocytes per well. The selected recloned hybridoma cell lines were expanded in culture flasks containing Dulbecco's Modified Eagle's medium supplemented with 10 agamma horse serum, 2 mM L-glutamine, and 1 mM sodium pyruvate.

EXAMPLE 7

Monoclonal Antibody Purification

Monoclonal antibody was purified from culture media containing 10% agamma horse serum. Briefly, immunoglobulin was precipitated with 50% $(NH_4)_2SO_4$ at pH 7.0, resolubilized in distilled $H_2O$, and reprecipitated with polyethylene glycol (7000–9000) at 13% (w/v) final concentration. The polyethylene glycol precipitate was solubilized in 0.02 M $PO_4$, pH 5.6, and applied to a CM-cellulose (Whatman, Clifton, NJ.) column equilibrated in the same buffer. Adsorbed immunoglobulin was eluted with 0.02M $PO_4$, pH 7.8, plus 0.2 M NaCl, dialyzed against 0.01M $PO_4$, pH 8.0, and applied to a DEAE-cellulose (Whatman) column equilibrated with the latter buffer. Adsorbed antibody was eluted with 0.025M $PO_4$, pH 8.0, equilibrated against PBS, and concentrated by ultrafiltration (Amicon, Danvers, MA.). The purified monoclonal antibodies were radioiodinated by the chloramine-T method to a specific activity of 5 to 10 μCi/ ‖ g. In addition to mpouse IgG, the purified antibody contained 10 to 40% horse immunoglobulin as determined by binding of the radioiodinated preparation to solid-phase goat anti-horse IgG. The percentage of monoclonal anti-CEA antibody in the preparation was determined by binding of the radioiodinated antibody to a CEA immunoadsorbent, as described in Primus et al., J. Immunol. 118:55, 1977.

Antibody isotype was determined by double immunodiffusion with class and subclass specific antisera (Litton Bionetics, Kensington, MD).

EXAMPLE 8

RIA (Radioimmunoassay)

Two types of RIAs were used, differing in the method of separating bound and free labeled antigen. Assay of supernatant media from hybridoma cultures for anti-CEA and anti-MA antibody activity used the Z-gel method described by Hansen et al. in Human Pathol. 5:139, 1974. Binding studies of selected monoclonal antibodies with CEA and MA, and all assays for NCA reactivity, used a solid-phase double antibody procedure (Newman et al., Proc. Am. Assoc. Cancer Res. 21:218, 1980). The basic assay consisted of 2.0 ml of 0.01M $NH_4Ac$, pH 6.25, containing 1.0% normal rabbit serum, about 0.5 ng of labeled antigen (30 to 50 μCi/μg) and 0.05 ml aliquots of antibody preparations. Incubations at 45° for 1 hr were used for the detection of CEA and MA antibody activity in hybridoma culture media while 4 hr incubations at the same temperature were used for the detection of NCA antibody. Labeled antigen binding curves and competitive-inhibition determinations were derived after incubation for 4 hr at 45° and 24 hr at room temperature, respectively. After incubation, 1.0 ml of Z-gel or solid-phase anti-immunoglobulin, GAM or DAG, was added and the tubes mixed. Tubes receiving Z-gel were centrifuged immediately while an additional 15 min incubation at room temperature was carried out for tubes receiving GAM or DAG. Tubes were washed once with 2.0 ml of 0.1M $NH_4Ac$ (Z-gel assays) or PBS (double antibody assays) before counting. Nonspecific binding was 10% and 1% for Z-gel and double antibody assays, respectively. Monoclonal antibody, goat antisera, unlabeled antigen, and labeled antigen were diluted in PBS containing 1.0% human serum albumin.

EXAMPLE 9

Antibody Affinity Determination

Antibody affinity was determined by the competitive RIA method of Muller in J. Immunol. Methods 34:345, 1980. The product of the calculated association constant and antibody concentration was less than 10, as recommended by Jacobsen et al. in J. Immunol. Methods 50:77, 1982.

EXAMPLE 10

Blocking Assays

Reciprocal blocking experiments used a solid-phase competitive sandwich procedure. Polyclonal goat anti-CEA serum was bound to vinylidine fluoride powder (Kynar, grade 301F; Pennwalt Corp., King of Prussia, Pa.) and sensitized with unlabeled CEA by incubation for 1 hr at 45° in 0.01M NH$_4$Ac. The amount of CEA used bound 40% of the maximal amount of bindable radiolabeled monoclonal antibody. The CEA-sensitized Kynar, 0.5 ml, was incubated with 0.05 ml aliquots of monoclonal antibody dilutions for 1 hr at 45°, centrifuged, and the pellet resuspended in 1.0 ml of 0.01M NH$_4$Ac containing 1%, normal rabbit serum. Radioiodinated monoclonal antibody contained in 0.05 ml was added to the tubes, incubated for 1 hr at 45°, centrifuged, washed once, and the pellet then counted. Nonspecific binding to unsensitized Kynar of the labeled antibody preparations was less than 5%.

EXAMPLE 11

Erythrocyte Binding

Erythrocytes from A, B, and O secretor and non-secretor individuals were combined in equal proportions as a 2% or 10% suspension and incubated for 1 hr at room temperature with 50 $\mu$l aliquots of hydridoma tissue culture medium. The cells were washed, resuspended in PBS, and incubated for 1 hr at room temperature with radioiodinated affinity-purified GAM having heavy and light chain specificities. After incubation, the cells were washed and counted.

EXAMPLE 12

Tissue Processing and Fixation

Tissues were obtained from 23 individuals with colorectal cancer. Of these adenocarcinomas, 3 were in the cecum, 6 in the ascending colon, and 14 i the rectosigmoid. One was poorly differentiated whereas the remaining were moderately well differentiated. Morphologically normal mucosa adjacent to the tumor and/or at resection margins was available in 21 of these cases. The Dukes' classification was used for clinical staging (Dukes, G. E., J. Pathol. Bacteriol. 35:322, 1932).

Surgical specimens were routinely fixed in 10% buffered formalin, pH 7.2, while in 6 cases, they were also fixed in EA as previously described in Primus et al., J. Natl. Cancer Inst. 67:10, 1981. Tissues were embedded in paraffin and serially sectioned at 5 $\mu$m in thickness. The sections were mounted on gelatinized slides, deparaffinized with xylene, and rehydrated with decreasing ethanol concentrations and, finally, PBS.

EXAMPLE 13

Immunohistochemical Procedures

A BRAB immunoperoxidase method was used for most of the staining reactions with goat an monoclonal antibodies (Guesdon et al., J. Histochem. Cytochem. 27:1131, 1979). The basic procedure with goat antibodies consisted of the sequential application of primary goat antibody, biotinylated rabbit anti-goat IgG (50 $\mu$g/ml), free avidin (100 $\mu$g/ml), and biotinylated horseradish peroxidase (50 $\mu$g/ml). Biotinylated reagents and avidin were obtained from Vector Laboratories (Burlingame, CA). All reagents were diluted in PBS except avidin which was diluted in 0.05M Tris, pH 8.6, plus 0.15M NaCl. The basic procedure was modified for the detection of antigen with murine monoclonal antibodies by the introduction of an affinity-purified goat anti-mouse IgG (30 $\mu$g/ml) step after the initial application of the monoclonal antibody. All immune and biotin-avidin reactions were carried out in a himidified atmosphere for 20 min at 37° and 30 min at room temperature, respectively. Each step was followed by two 5-min washes in PBS. One section on each slide received the test antibody while an adjacent section was exposed to a control preparation. The goat anti-CEA and -NCA antisera were used at a 1/600 and 1/100 dilution, respectively. Controls for these antisera consisted of similarly diluted antigen-neutralized CEA antiserum and/or normal goat serum. The monoclonal antibodies were used at 5 $\mu$g/ml, and normal mouse IgG (Pel-Freeze, Rogers, AR), 50 $\mu$g/ml, as well as antigen-neutralized purified monoclonal antibodies and ascites fluid were used for control purposes. Before application of the primary antibody, hydrated sections were incubated in 3% H$_2$O$_2$ in methanol, washed in PBS, and then incubated for 10 min at 37° with diluted normal rabbit serum. After the biotinylated enzyme step, the histochemical reaction was developed with 0.01% diaminobenzidine and 0.003% H$_2$O$_2$ in 0.05M Tris-HCl, pH 7.6, at room temperature for 15 min. Immunoperoxidase-stained slides were counterstained lightly with Harris's hematoxylin.

An unlabeled antibody method using glucose oxidase-antiglucose oxidase complexes (Clark et al., J. Histochem. Cytochem. 30:27, 1982) was used for the detection of NCA in neutrophils. The basic procedure was similar to the BRAB technique except donkey anti-goat IgG and goat antiglucose oxidase-glucose oxidase complexes were substituted for biotinlylated rabbit anti-goat IgG and biotinylated horseradish peroxidase, respectively. The avidin and H$_2$O$_2$ steps were also omitted, and preincubation with undiluted normal horse serum was used instead of normal rabbit serum. The enzymatic disclosing reaction consisted of the following: 6.7 mg/ml $\beta$-D-glucose (Calbiochem-Behringer, LaJolla, CA), 0.67 mg/ml NBT (Research Organics Incs., Cleveland, OH), and 0.0167 mg/ml phenazine methosulfate (Sigma, St. Louis, MO) in 0.05M Tris, pH 8.3. The glucose and NBT were preheated to 37° for 1 hr, at which point the phenazine methosulfate and the tissue sections were added. After further incubation for 45 min at 37°, the slides were washed and counterstained with nuclear fast red.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An immunoassay method for determining carcinoembryonic antigen (CEA) in an unextracted serum or plasma sample, said method comprising the steps of:
    (1) contacting an unextracted serum or plasma sample with a capture antibody bound to a solid support, for a time sufficient to permit antibody binding to CEA in said sample, said capture antibody being a hybridoma-derived Class I anti-CEA monoclonal antibody which specifically binds to an epitope shared by CEA, meconium antigen and non-specific crossreacting antigen; and (2) contacting the resultant solid support, having the CEA bound to said capture antibody therreon, with a detectably labeled anti-CEA probe antibody whose binding to CEA is not appreciably ionic strength-dependent, for a time sufficient for the probe antibody to bind to CEA bound to said capture antibody, and determining the extent of binding of said probe antibody to said bound CEA, wherein said probe antibody is either:

(a) a hybridoma-derived Class II anti-CEA monoclonal antibody which specifically binds to an epitope shared by CEA and meconium antigen, but which does not specifically bind to non-specific crossreacting antigen, wherein binding to said epitope cannot be cross-blocked by a hybridoma-derived Class I anti-CEA monoclonal antibody which specifically binds to an epitope shared by CEA, meconium antigen and non-specific crossreacting antigen; or (b) a hydridoma-derived Class III anti-CEA monoclonal antibody which specifically binds to an epitope on CEA and does not specifically bind to meconium antigen or non-specific crossreacting antigen.

2. The method of claim 1, wherein said probe antibody is said hybridoma-derived Class II anti-CEA monoclonal antibody which specifically binds to an epitope shared by CEA and meconium antigen, but which does not specifically bind to non-specific crossreacting antigen, wherein binding to said epitope cannot be cross-blocked by a hybridoma-derived Class I anti-CEA monoclonal antibody which specifically binds to an epitope shared by CEA, meconium antigen and non-specific crossreacting antigen.

3. The method of claim 1, wherein said probe antibody is said hybridoma-derived Class III anti-CEA monoclonal antibody which specifically binds to an epitope on CEA and does not specifically bind to meconium antigen or non-specific crossreacting antigen.

4. The method of claim 1, wherein said probe antibody is labeled with a radioisotope, a fluorescent marker or an enzyme.

5. An immunoassay kit, suitable for determining the amount of carcinoembryonic antigen (CEA) in an unextracted serum or plasma sample, comprising amounts sufficient to perform said immunoassay of:

(1) a capture antibody bound to a solid support, said capture antibody being a hybridoma-derived Class I anti-CEA monoclonal antibody which specifically binds to an epitope shared by CEA, meconium antigen and non-specific crossreacting antigen; and (2) a detectably labeled anti-CEA probe antibody whose binding to CEA is not appreciably ionic strength-dependent, said probe antibody being different from said capture antibody and being either:

(a) a hybridoma-derived Class II anti-CEA monoclonal antibody which specifically binds to an epitope shared by CEA and meconium antigen, but which does not specifically bind to non-specific crossreacting antigen, wherein binding to said epitope cannot be cross-blocked by a hybridoma-derived Class I anti-CEA monoclonal antibody which specifically binds to an epitope shared by CEA, meconium antigen and non-specific crossreacting antigen; or (b) a hybridoma-derived Class III anti-CEA monoclonal antibody which specifically binds to an epitope on CEA and does not specifically bind to meconium antigen or non-specific crossreacting antigen.

6. The kit of claim 5, wherein said probe antibody is said hybridoma-derived Class II anti-CEA monoclonal antibody which specifically binds to an epitope shared by CEA and meconium antigen, but which does not specifically bind to non-specific crossreacting antigen, wherein binding to said epitope cannot be cross-blocked by a hybridoma-derived Class I monoclonal antibody which specifically binds to an epitope shared by CEA, meconium antigen and non-specific crossreacting antigen.

7. The kit of claim 5, wherein said probe antibody is said hybridoma-derived Class III anti-CEA monoclonal antibody which specifically binds to an epitope on CEA and does not specifically bind to meconium antigen or non-specific crossreacting antigen.

8. The kit of claim 5, wherein said probe antibody is labeled with a radioisotope, a fluorescent marker or an enzyme.

9. A essentially purified hybridoma-derived monoclonal antibody which specifically binds to an epitope on carbinoembryonic antigen (CEA), said antibody being a Class III anti-CEA monoclonal antibody which specifically binds to an epitope on 200,000 dalton CEA, but does not specifically bind to either meconium antigen or non-specific crossreacting antigen.

* * * * *

UNITED STATES PATENT AND TRADEMARK OFFICE
CERTIFICATE OF CORRECTION

| | | |
|---|---|---|
| PATENT NO. | : 4,818,709 | Page 1 of 1 |
| DATED | : April 4, 1989 | |
| INVENTOR(S) | : Frederick J. Primus and Milton D. Goldenberg | |

It is certified that error appears in the above-identified patent and that said Letters Patent is hereby corrected as shown below:

<u>Column 28,</u>
Line 46, change "carbinoembryonic" to -- carcinoembryonic --.

Signed and Sealed this

Twenty-ninth Day of April, 2003

JAMES E. ROGAN
*Director of the United States Patent and Trademark Office*